United States Patent
Nihei et al.

(10) Patent No.: US 8,083,054 B2
(45) Date of Patent: Dec. 27, 2011

(54) HOUSING CONTAINER FOR IMPLANT FIXTURE

(75) Inventors: Kinya Nihei, Itabashi-ku (JP);
Tatsunosuke Miyano, Itabashi-ku (JP);
Yoshihiro Sakaguchi, Itabashi-ku (JP);
Makoto Michiaki, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/084,037

(22) Filed: Apr. 11, 2011

(65) Prior Publication Data
US 2011/0247947 A1   Oct. 13, 2011

(30) Foreign Application Priority Data
Apr. 13, 2010   (JP) .................................. 2010-092294

(51) Int. Cl.
*A61C 19/02* (2006.01)
*B65D 83/10* (2006.01)

(52) U.S. Cl. ............ 206/63.5; 206/368; 433/9; 433/173

(58) Field of Classification Search .............. 206/63.5, 206/368, 369, 339, 453, 493, 521, 583, 586, 206/588; 433/8, 9, 173, 229
See application file for complete search history.

(56) References Cited

U.S. PATENT DOCUMENTS

| | | | | |
|---|---|---|---|---|
| 2,136,352 | A * | 11/1938 | L'Hommedieu | 206/63.5 |
| 5,062,800 | A * | 11/1991 | Niznick | 206/368 |
| 5,368,160 | A * | 11/1994 | Leuschen et al. | 206/339 |
| 5,560,487 | A * | 10/1996 | Starr | 206/583 |
| 6,217,332 | B1 * | 4/2001 | Kumar | 433/173 |
| 6,309,220 | B1 * | 10/2001 | Gittleman | 433/173 |
| 7,819,915 | B2 * | 10/2010 | Stobie et al. | 623/2.11 |
| 7,921,991 | B2 | 4/2011 | Sato et al. | |
| 2008/0217190 | A1 * | 9/2008 | Matsushige et al. | 206/63.5 |

* cited by examiner

*Primary Examiner* — Luan K Bui
(74) *Attorney, Agent, or Firm* — Oblon, Spivak, McClelland, Maier & Neustadt, L.L.P.

(57) ABSTRACT

To minimize used titanium materials, a container for an implant fixture has a housing main body 1, an implant fixture holding member 2, and a cap 3, the main body 1 is made of glass or the like and has guide grooves 1a in an axial direction, the holding member 2 is made of titanium and includes a bottom part 2a contacting with a top of a dental implant fixture X, and three or more guide parts 2b surrounding the fixture X, the guide part 2b has an insertion lock part 2ba to be locked in the guide groove 1a, the cap 3 is made of a resin, has a press part 3a, and seals the upper surface of the main body 1, and the press part 3a contacts with an engagement hole Xa and/or an upper surface Xb of the fixture X to press the fixture X.

2 Claims, 4 Drawing Sheets

HOUSING CONTAINER FOR IMPLANT FIXTURE

BACKGROUND OF THE INVENTION

1. Field of the Invention

The present invention relates to a housing container for an implant fixture to house a dental implant fixture used in a dental implant treatment.

2. Description of the Conventional Art

One of recently prevailing dental prosthesis treatments is a dental implant treatment in which a dental implant fixture made of titanium or a titanium alloy having excellent biocompatibility is embedded in a jawbone at a lost tooth position, and is used instead of a natural dental root through a direct bond with the bone (osseo-integration). The dental implant fixture used in the dental implant treatment is configured separately from an abutment for fixing a dental prosthesis, or is configured integrally with the abutment.

The dental implant fixture is strongly required to be sanitary because of being embedded in a jawbone. Thus, a housing container for an implant fixture to house a dental implant fixture until being used it is also strongly required to have high sealability to secure a sterilized condition.

As for a housing container for an implant fixture capable of securing a sterilized condition and having high sealability, for example, Japanese Patent Application Laid-Open No. 2008-284145 discloses a housing container in which a housing main body is made of a titanium material, which is a same material as that of the dental implant fixture, in order to make impurities hardly adhere to the dental implant fixture. However, since this housing container for an implant fixture has the housing main body made of a titanium material, there is a problem of wasting titanium resources when considering a fact that the housing container for an implant fixture is a disposable.

Japanese translation of PCT Publication No. 2000-512194, Japanese Translation of PCT Publication No. 2004-526530, and Japanese Patent Application Laid-Open No. 2008-125982, for example, disclose housing containers for an implant fixture to solve the aforementioned problem. The housing container for an implant fixture has a housing main body made of a resin, and houses a dental implant fixture by engaging a fixture mount in advance with an intraoral side end portion of a dental implant fixture and hanging the dental implant fixture with the fixture mount. In this housing container for an implant fixture, the dental implant fixture is hung with the fixture mount, and an outer surface of the dental implant fixture is not in contact with an inner surface of the housing main body. Thus, the housing main body has advantages that it does not need to be made of titanium, and the dental implant fixture is hardly damaged during conveyance. However, there are problems that this housing container for an implant fixture needs many parts for hanging the dental implant fixture and in addition, since the fixture mount needs to be removed after the dental implant fixture is embedded, it takes much time and work.

Japanese Patent Application Laid-Open No. 2004-243127 and Japanese Translation of PCT Publication No. 2004-510541, for example, disclose housing containers for an implant fixture to solve the aforementioned problems. The housing container for an implant fixture includes a holder part in a housing main body instead of a fixture mount, and houses a dental implant fixture by holding an intraoral side end portion of the dental implant fixture with the holder part. In these housing containers for an implant fixture, the intraoral side end portion of the dental implant fixture is held with the holder part, and an outer surface of the dental implant fixture is not in contact with an inner surface of the housing main body. Thus, the housing main body has advantages that it does not need to be made of titanium, and the dental implant fixture is hardly damaged during conveyance. In addition, the housing container for an implant fixture has an advantage that it does not use a fixture mount, and thus the dental implant fixture can be directly taken out by a tool. However, there is a problem that, since holder part holds the intraoral side end portion of the dental implant fixture, when the dental implant fixture is taken out from the holder part, an outer surface of the dental implant fixture could be damaged because of scraping against the holder part. Further, in the housing container for an implant fixture, there is a problem that an outer diameter of a collar part provided at the intraoral side end portion of the dental implant fixture should be bigger than an outer diameter of an embedding portion in order to hold the dental implant fixture with the holder part, and thus the housing container for an implant fixture cannot house a dental implant fixture having the outer diameter of the collar part which is equal to the outer diameter of the embedding portion.

SUMMARY OF THE INVENTION

Problems to be Solved by the Invention

In view of the problems mentioned above, the present invention is directed to a housing container for housing a dental implant fixture, which is made with a minimum titanium material for not wasting titanium resources, can accurately and easily fix various kinds of dental implant fixtures, and does not damage the housed dental implant fixture when the dental implant fixture is conveyed or taken out.

Means for Solving the Problem

Present inventors carried out earnest works to solve the aforementioned problems, and as a result, they found out the followings to complete the present invention. A housing container for an implant fixture includes a container-like housing main body, an implant fixture holding member, 1 and a cap. The container-like housing main body is made of glass or a resin, has at least one or more guide grooves having a predetermined length and has an opening upper surface. The guide grooves are provided in parallel with an axial direction from a cylindrical inner surface upper part of the container-like housing main body. The implant fixture holding member is made of titanium or a titanium alloy, and configured with a bottom part to be in contact with a top end part of a dental implant fixture, and at least three or more guide parts erected from the bottom part so as to be positioned around an outer surface of the dental implant fixture. On an outer surface of one or more of the guide parts, an insertion lock part is formed to be inserted and locked in the guide groove of the housing main body, so that the implant fixture holding member is inserted and held in the housing main body. The cap is made of a resin, has a press part, and seals the upper surface of the housing main body. The press part is inserted into an engagement hole so as to be in contact with the dental implant fixture whose top end part is in contact with the bottom part of the implant fixture holding member, and/or is in contact with an upper surface on the intraoral side, to thereby press the intraoral side of the dental implant fixture. The engagement hole is formed in the intraoral side of the dental implant fixture so as to be engaged with a tool for embedding it into a jawbone. In this housing container for an implant fixture configured as mentioned above, titanium materials are necessarily used only for the implant fixture holding member configured with the bottom part and a guide part. The bottom part is in direct contact with a portion of the dental implant fixture which is to be embedded in an alveolar ridge, and the guide part could be in contact with a portion of the dental implant fixture which is to be embedded in an alveolar ridge. Thus, the housing container for an implant fixture can prevent wasting of titanium resources. Further, the housing container for an implant fixture holds and fixes the dental implant fixture with both the press part of the cap and the bottom part of the implant fixture holding member. Thus, the housing container for an implant fixture can accurately and easily positions and fixes various kinds of dental implant fixtures. In addition, the guide part is provided to be positioned around the outer surface of the dental implant fixture. Thus, the positioned and fixed dental implant fixture does not move greatly in the housing main body during conveyance, so that the dental implant fixture is not damaged. Furthermore, after the housing container for a dental implant fixture is opened, the positioned and fixed dental implant fixture can be easily taken out directly by a tool for embedding the dental implant fixture into a jawbone without contacting other portions in the housing main body.

According to an aspect of the present invention, a housing container for an implant fixture includes a container-like housing main body, an implant fixture holding member, and a cap. The container-like housing main body is made of glass or a resin, has at least one or more guide grooves having a predetermined length and has an opening upper surface. The guide grooves are provided in parallel with an axial direction from a cylindrical inner surface upper part. The implant fixture holding member is made of titanium or a titanium alloy, and is configured with a bottom part to be in contact with a top end part of a dental implant fixture, and at least three or more guide parts erected from the bottom part so as to be positioned around an outer surface of the dental implant fixture. On the outer surface of one or more of the guide parts, an insertion lock part is formed to be inserted and locked in the guide groove of the housing main body, so that the implant fixture holding member is inserted and held in the housing main body. The cap is made of a resin, has a press part, and seals the upper surface of the housing main body. The press part is inserted into an engagement hole so as to be in contact with the dental implant fixture whose top end part is in contact with the bottom part of the implant fixture holding member, and/or is in contact with an upper surface on the intraoral side, to thereby press the intraoral side of the dental implant fixture. The engagement hole is formed in the intraoral side of the dental implant fixture so as to be engaged with a tool for embedding the dental implant fixture into a jawbone.

Furthermore, the press part of the cap is made of titanium or a titanium alloy. Thus, when a dental implant fixture whose upper surface on the intraoral side is in direct contact with a jawbone at a time of embedding the dental implant fixture is housed, impurities hardly adhere to the dental implant fixture, so it is preferable.

Effect of the Invention

In the housing container of an implant fixture according to the present invention configured as mentioned above, titanium materials are used only for the implant fixture holding member configured with the bottom part and a guide part. The bottom part is in direct contact with a portion of the dental implant fixture which is to be embedded in an alveolar ridge, and the guide part could be in contact with a portion of the dental implant fixture which is to be embedded in an alveolar ridge. Thus, it is possible to minimize the use of titanium material and prevent wasting of titanium resources. Further, the housing container for an implant fixture holds and fixes the dental implant fixture with both the press part of the cap and the bottom part of the implant fixture holding member, instead of fixing the implant fixture by the outer periphery of the implant fixture or a fixture mount. Thus, the housing container for an implant fixture can accurately and easily positions and fixes various kinds of dental implant fixtures. In addition, the guide parts are provided to be positioned around the outer surface of the dental implant fixture. Thus, the positioned and fixed dental implant fixture does not move greatly in the housing main body during conveyance, so that the dental implant fixture is not damaged. Furthermore, after the housing container for a dental implant fixture is opened, the positioned and fixed dental implant fixture can be easily taken out directly by a tool for embedding the dental implant fixture into a jawbone without contacting other portions in the housing main body.

Furthermore, the press part of the cap is made of titanium or a titanium alloy. Thus, when a dental implant fixture whose upper surface on the intraoral side is in direct contact with a jawbone at a time of embedding the dental implant fixture is housed, impurities hardly adhere to the dental implant fixture, so it is preferable.

DETAILED DESCRIPTION OF PREFERRED EMBODIMENT

In these drawings, a dental implant fixture X includes an engagement hole Xa on the intraoral side, and the engagement hole Xa engages with a tool for embedding the dental implant fixture X into a jawbone. The dental implant fixture X is taken out from a housing container for an implant fixture according to the present invention as mentioned below by the tool for embedding the dental implant fixture into a jawbone being used, after opening of the housing container for an implant fixture. The dental implant fixture X is configured separately from an abutment for fixing a dental prosthesis, or is configured integrally with the abutment.

Figure 1:
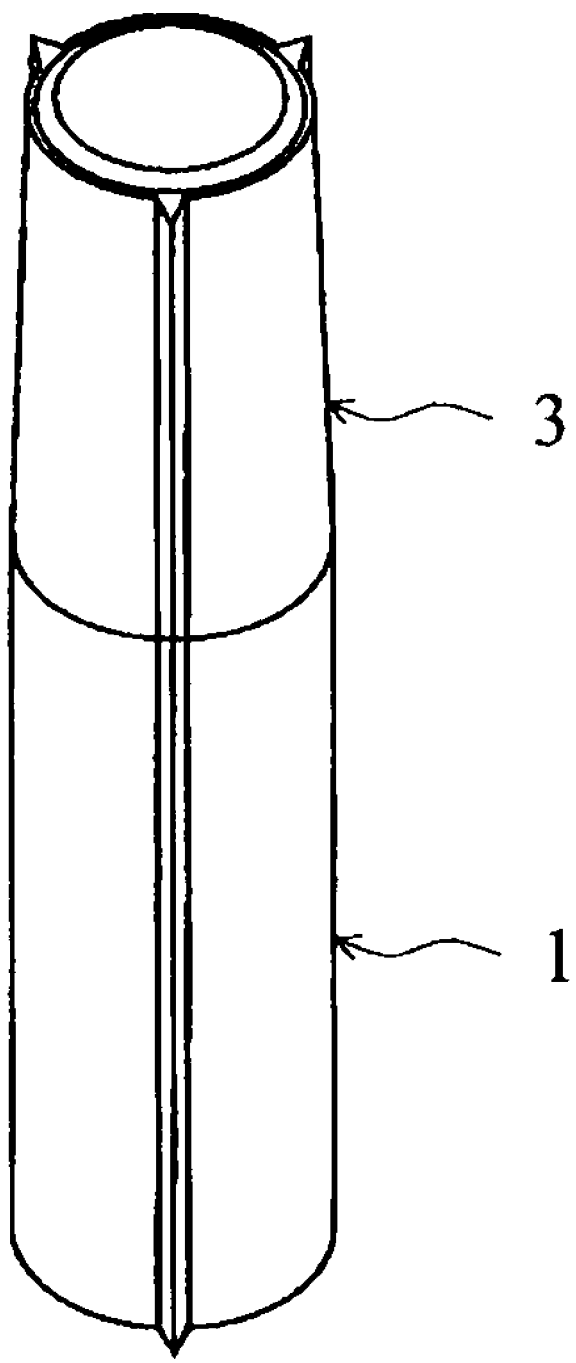
FIG. 1 is a perspective view illustrating one example of a housing container for an implant fixture according to the present invention in which a dental implant fixture is housed.
Figure 2:
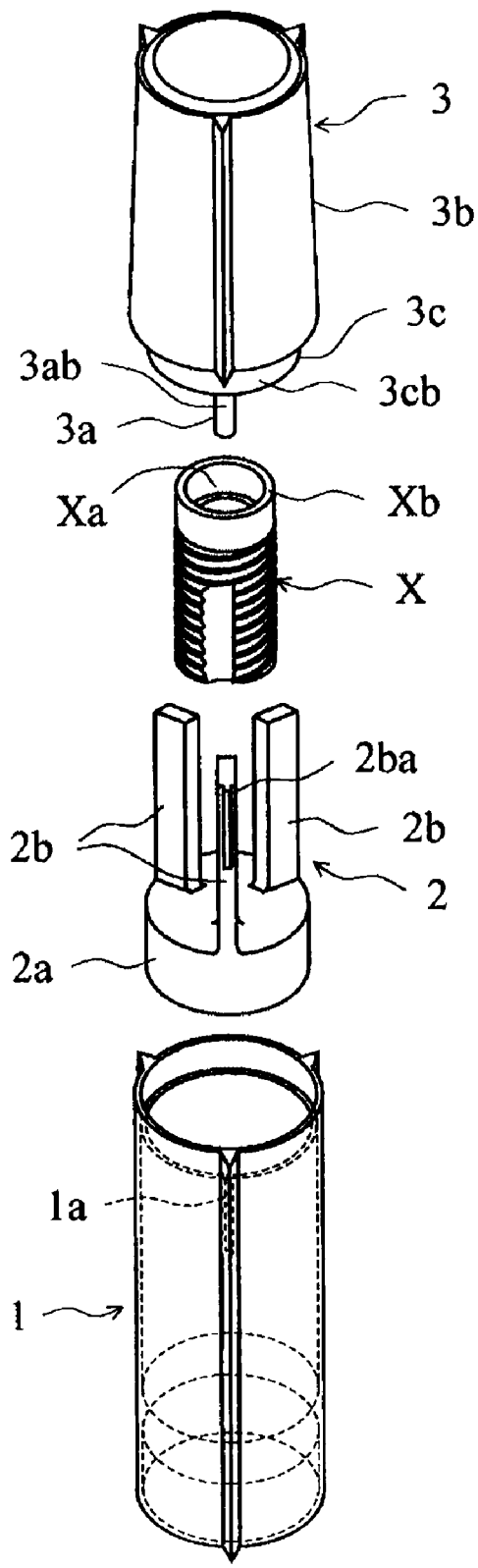
FIG. 2 is a perspective view illustrating a disassembly state of the housing container for an implant fixture of FIG. 1.

The housing container for an implant fixture according to the present invention houses the dental implant fixture X. As illustrated in FIG. 2, the housing container for an implant fixture is configured with a housing main body 1 to be a base body, an implant fixture holding member 2 to be inserted and held in the housing main body 1, and a cap 3 for sealing an upper surface of the housing main body 1.

The housing main body 1 has a bottomed container shape having an opening upper surface. The housing main body 1 is made of glass or a resin because of not being in direct contact with the dental implant fixture X. Further, the inner surface of the housing main body has a cylindrical shape, and includes at least one or more guide grooves 1a provided in parallel with the axial direction from the upper part of the inner surface of the housing main body 1. The one or more guide grooves 1a are provided for equipping the implant fixture holding member 2 in the housing main body 1. The length of the guide groove 1a is set, corresponding to the length of an insertion lock part 2ba of a guide part 2b of the implant fixture holding member 2 described below. In addition, in the present exemplary embodiment, since a cap fitting part 3c of the cap 3 fits to the upper surface of the housing main body 1 so as to seal the upper surface, an inner diameter of the upper surface opening part of the housing main body is set to be bigger than other portions (refer to FIGS. 2 and 3).

The implant fixture holding member 2 is configured with a bottom part 2a and at least three or more guide parts 2b erected from the bottom part 2a. As for the implant fixture holding member 2, the bottom part 2a functions for positioning and fixing the top end side of the dental implant fixture X. The guide parts 2b are located around the outer surface of the dental implant fixture X so as to prevent the dental implant fixture X from being damaged during conveyance, and have a function that the dental implant fixture X can be easily taken out directly by a tool for embedding the dental implant fixture into a jawbone, without contacting other portions in the housing main body 1. Thus, the implant fixture holding member 2 is made of titanium or a titanium alloy (refer to FIG. 3). Further, for inserting and holding the implant fixture holding member 2 in the housing main body 1, the insertion lock part 2ba inserted and locked in the guide groove 2a of the housing main body 1 is formed to project from the outer surface on the side of the housing main body 1 of the one or more guide parts 2b (refer to FIG. 4).

Figure 3:
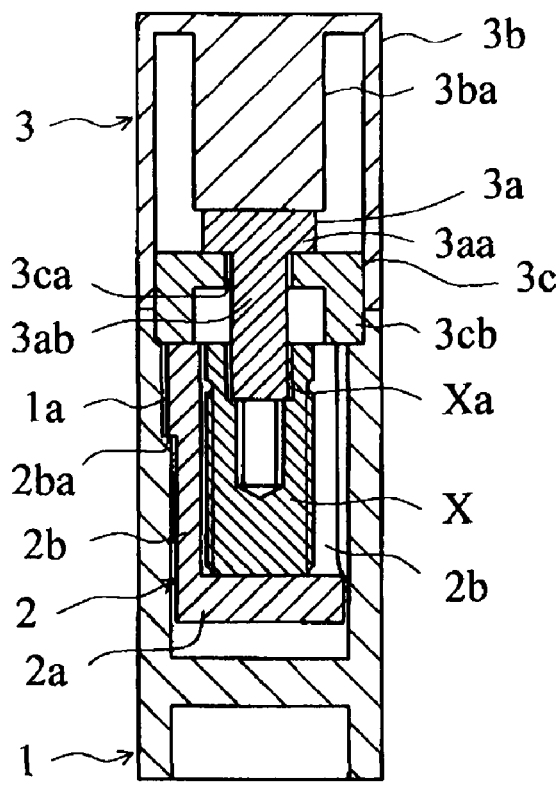
FIG. 3 is a longitudinally sectional view of FIG. 1.
Figure 4:
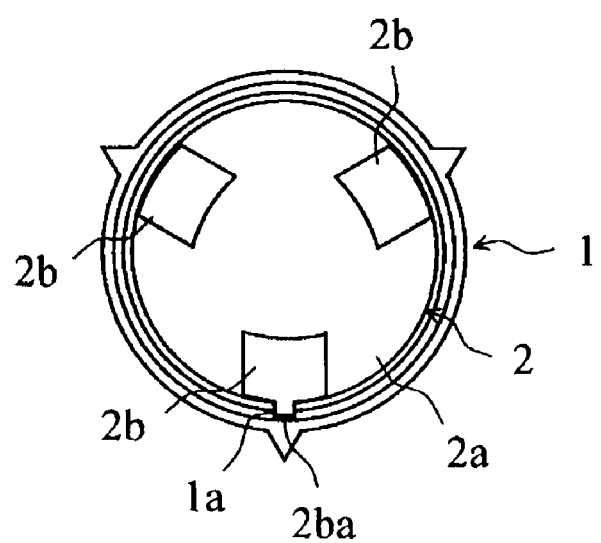
FIG. 4 is a plan view illustrating a state that an implant fixture holding member is inserted and held in a housing main body.

The cap 3 includes a press part 3a. The press part 3a is inserted into the engagement hole Xa of the dental implant fixture X so as to be in contact with the dental implant fixture X as illustrated in FIG. 3, where the engagement hole Xa engages with a tool for embedding the dental implant fixture X into a jawbone. Or, although the configuration is not illustrated, the press part 3a is in contact with an upper surface Xb on the intraoral side of the dental implant fixture X. Or, although the configuration is not illustrated, the press part 3a is inserted into the engagement hole Xa provided on the intraoral side of the dental implant fixture X so as to be in contact with the dental implant fixture X and is simultaneously in contact with the upper surface Xb on the intraoral side, where the engagement hole Xa engages with a tool for embedding the dental implant fixture X into a jawbone. By providing the press part 3a with the above configuration, the intraoral side of the dental implant fixture X is positioned and fixed. As for the cap 3, although the press part 3a is in direct contact with the dental implant fixture X, the contacting part is not a portion to be embedded into an alveolar ridge of the dental implant fixture X, but a portion in the engagement hole Xa for the tool for embedding the dental fixture X into a jawbone, and/or the upper surface Xb on the intraoral side. Thus, the press part 3a can be made of a resin. However, if the upper surface Xb on the intraoral side of the dental implant fixture X could be in direct contact with a jawbone, at least the press part 3a is preferably made of titanium or a titanium alloy for preventing impurities from adhering. In addition, in the present exemplary embodiment, the cap 3 illustrated in the drawings is configured with a tack-shaped press part 3a, a cap main body part 3b, and a cap fitting part 3c. The tack-shaped press part 3a includes a flange part 3aa and a pin part 3ab which is erected from a center part of the flange part 3aa. The cap main body part 3b has a press part supporting part 3ba erected from a center part of the inner surface side of the upper surface. The cap fitting part 3c has, at the center part of the upper surface, a through hole 3ca in which the pin part 3ab of the press part 3a fits, and fits to the inner surface of the cap main body part 3b. Then the press part supporting part 3ba of the cap main body part 3b and the upper surface of the cap fitting part 3c hold the flange part 3aa of the press part 3a. However, the cap 3 is not restricted in the example illustrated in the drawings. For example, the cap 3 can be produced by integrating the above-described parts when it is made of a resin.

Figure 5:
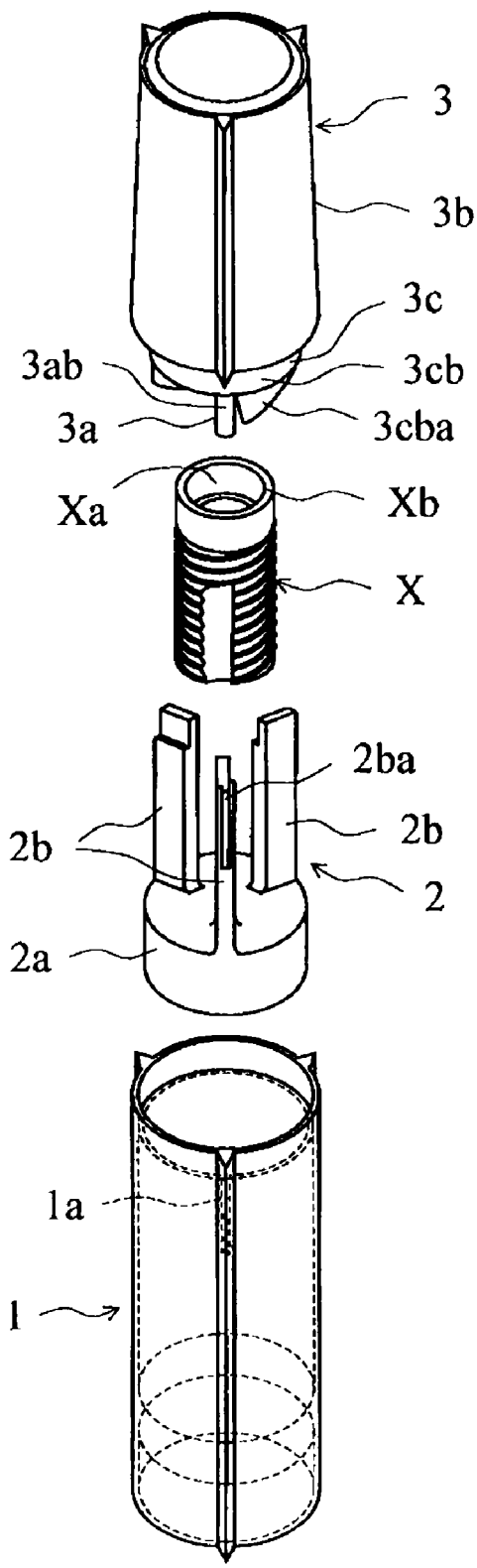
FIG. 5 is a perspective view illustrating a disassembly state of another example of a housing container for an implant fixture according to the present invention for housing a dental implant fixture.

In the present exemplary embodiment, a lower part of the cap fitting part 3c has a projecting part 3cb which projects from the cap main body part 3b when the cap fitting part 3c fits to the cap main body part 3b. The projecting part fits to the upper surface opening part of the housing main body 1, so that the cap 3 seals the upper surface of the housing main body 1 (refer to FIGS. 2 and 3). Further, when the cap 3 seals the upper surface of the housing main body 1, the projecting part 3cb is in contact with top ends of the respective guide parts 2b of the implant fixture holding member 2 attached to the housing main body 1. Thus, the implant fixture holding member 2 is not longitudinally moved in the housing main body 1. Furthermore, as illustrated in FIG. 5, faces of the top end parts of the respective guide parts 2b of the implant fixture holding member 2 are cut out, and a plurality of convex parts 3cba of the projecting part 3cb are engaged with ends of the cut out parts of the respective guide parts 2b. The convex part 3cba has inclined face in the periphery direction and is provided at an inner edge of the projecting part 3cb of the cap fitting part 3c. Thus, dental implant fixture X can be easily taken out from the upper surface of the housing main body 1 when cap 3 in a state of being fitted is rotated. In addition, a sealing method of the upper surface of the housing main body 1 with the cap 3 is not restricted to the example in the drawings and, for example, screwing or the like can be used.

The housing container for an implant fixture according to the present invention houses the dental implant fixture X with the housing main body 1 and the cap 3 with high sealability, where the housing main body 1 is a base body, and the cap 3 seals the upper part of the housing main body 1. Thus, the dental implant fixture X can secure a sterilized condition until a time just before performing of a dental implant treatment. Further, in the housing container for an implant fixture, titanium materials are used only for the implant fixture holding member 2, which is configured with the bottom part 2a and the guide part 2b and is inserted and held in the housing main body 1. The bottom part 2a is in direct contact with a portion of the dental implant fixture X which is to be embedded in an alveolar ridge, and the guide part 2b could be in contact with a portion of the dental implant fixture X which is to be embedded in an alveolar ridge. Thus, it is possible to minimize the use of titanium material and prevent wasting of titanium resources. Further, in the housing container for an implant fixture, the dental implant fixture X is not fixed with the outer surface thereof or the fixture mount, but is fixed to be held with the press part 3a of the cap 3 and the bottom part 2a of the implant fixture holding member 2. Thus, various types of dental implant fixtures X can be accurately and easily positioned and fixed. Further, in the housing container for an implant fixture, the guide parts 2b are provided to be located around the outer surface of the dental implant fixture X. Thus, the positioned and fixed dental implant fixture X does not move greatly and is not damaged even when a big impact is applied during conveyance. Furthermore, after the housing container for a dental implant fixture is opened, the positioned and fixed dental implant fixture X can be easily taken out directly by a tool for embedding the dental implant fixture X into a jawbone without contacting other portions in the housing main body 1, and the dental implant fixture X is not damaged owing to no friction with the housing container for an implant fixture.

In addition, the press part 3a of the cap 3 is made of titanium or a titanium alloy. Thus, when the dental implant fixture X whose upper surface on the intraoral side is in direct contact with a jawbone at a time of embedding the dental implant fixture X is housed, impurities hardly adhere to the dental implant fixture X, so it is preferable.

What is claimed is:

1. A housing container for an implant fixture comprising:
a container-like housing main body (1) which is made of glass or a resin, has at least one or more guide grooves (1a) having a predetermined length and being provided in parallel with an axial direction from a cylindrical inner surface upper part and has an opening upper surface;
an implant fixture holding member (2) which is made of titanium or a titanium alloy and comprises a bottom part (2a) to be in contact with a top end part of a dental implant fixture (X), and at least three or more guide parts (2b) erected from the bottom part (2a) so as to be positioned around an outer surface of the dental implant fixture (X), wherein, on the outer surface of one or more of the guide parts (2b), an insertion lock part (2ba) is formed to be inserted and locked in the guide groove (1a) of the housing main body (1), so that the implant fixture holding member (2) is inserted and held in the housing main body (1); and
a cap (3) being made of a resin, having a press part (3a), and sealing the upper surface of the housing main body (1), wherein the press part (3a) is inserted into an engagement hole (Xa) so as to be in contact with the dental implant fixture (X) whose top end part is in contact with the bottom part (2a) of the implant fixture holding member (2), and/or is in contact with an upper surface (Xb) on the intraoral side, to thereby press the intraoral side of the dental implant fixture (X), and wherein the engagement hole (Xa) is formed in the intraoral side of the dental implant fixture (X) so as to be engaged with a tool for embedding the dental implant fixture (X) into a jawbone.

2. The housing container for an implant fixture as claimed in claim 1, wherein the press part (3a) of the cap (3) is made of titanium or a titanium alloy.

* * * * *